(12) United States Patent
Talingting-Pabalan et al.

(10) Patent No.: US 8,133,924 B2
(45) Date of Patent: Mar. 13, 2012

(54) DEMULSIFIERS AND METHODS FOR USE IN PHARMACEUTICAL APPLICATIONS

(75) Inventors: Ruela Talingting-Pabalan, Burlington, NJ (US); Manilal S. Dahanayake, Princeton Junction, NJ (US); Gary Woodward, Northwich Cheshire (GB); Herve Adam, Clarksburg, NJ (US)

(73) Assignee: Rhodia Operations, Aubervilliers (FR)

( * ) Notice: Subject to any disclaimer, the term of this patent is extended or adjusted under 35 U.S.C. 154(b) by 250 days.

(21) Appl. No.: 12/384,262

(22) Filed: Apr. 2, 2009

(65) Prior Publication Data

US 2009/0209664 A1 Aug. 20, 2009

Related U.S. Application Data

(63) Continuation-in-part of application No. 12/191,130, filed on Aug. 13, 2008, now Pat. No. 7,671,099.

(60) Provisional application No. 60/955,551, filed on Aug. 13, 2007, provisional application No. 61/072,768, filed on Apr. 2, 2008.

(51) Int. Cl.
*B01D 17/05* (2006.01)
(52) U.S. Cl. .......... 516/181; 514/772; 514/784; 558/44; 558/251; 562/8; 568/687; 568/697; 568/852; 554/1
(58) Field of Classification Search ............. 516/81; 514/772, 784; 558/44, 251; 562/8; 568/687, 568/697, 852; 554/1
See application file for complete search history.

(56) References Cited

U.S. PATENT DOCUMENTS

| | | | |
|---|---|---|---|
| 3,756,959 A | 9/1973 | Vitalis et al. | 252/336 |
| 4,129,508 A | 12/1978 | Friihauf | 252/33 |
| 5,573,759 A | 11/1996 | Blank | 424/60 |
| 5,670,557 A | 9/1997 | Dietz et al. | 522/184 |
| 6,294,093 B1 | 9/2001 | Selvarajan et al. | 210/708 |
| 6,599,949 B2 | 7/2003 | Varadaraj et al. | 516/160 |
| 6,677,293 B1 | 1/2004 | Allgaier et al. | 510/417 |
| 2002/0055438 A1* | 5/2002 | Giard-Blanchard et al. | 507/100 |
| 2002/0161059 A1 | 10/2002 | Varadaraj et al. | 516/113 |
| 2003/0193110 A1 | 10/2003 | Yaritz et al. | 264/211 |
| 2005/0147750 A1* | 7/2005 | Jacobs et al. | 427/248.1 |
| 2006/0135628 A1* | 6/2006 | Newman et al. | 516/156 |
| 2006/0135683 A1 | 6/2006 | Adam et al. | 524/556 |
| 2006/0252805 A1* | 11/2006 | Horiuchi et al. | 514/355 |
| 2006/0260815 A1 | 11/2006 | Dahanayake et al. | 166/308.6 |

FOREIGN PATENT DOCUMENTS

DE 00/12660 3/2000

OTHER PUBLICATIONS

Angle (Encyclopedic Handbook of Emulsion Technology, Johan Sjöblom Ed., CRC Press 2001, Table 6, p. 579-581).*
FM Ghuiba & O M O Habib, H Kh Gharieb & B M Badran; "The Use of Egyptian Fusel Oil for the Preparation of Some Plasticizers Compatible with Polyvinyl Chloride"; Indian Journal of Technology, vol. 23, Aug. 1985, pp. 309-311.

* cited by examiner

*Primary Examiner* — Ling Choi
*Assistant Examiner* — Chun-Cheng Wang

(57) ABSTRACT

Demulsifiers containing an anionic surfactant selected from alkylsulfosuccinates, alkylsulfonates, alkylphosphonic acids, and their salts; a nonionic surfactant selected from ethylene oxide/propylene oxide copolymers, ethoxylated fatty acids of polyethylene glycol, terpene alkoxylates, and modified alkanolamides; or a combination of an anionic and a nonionic surfactant, and methods of use thereof in breaking emulsions.

25 Claims, No Drawings

DEMULSIFIERS AND METHODS FOR USE IN PHARMACEUTICAL APPLICATIONS

CROSS REFERENCE TO RELATED APPLICATIONS

This application is a continuation-in-part application of U.S. patent application Ser. No. 12/191,130, filed Aug. 13, 2008, which claims priority from U.S. Provisional Patent Application Ser. No. 60/955,551, filed Aug. 13, 2007, and also claims priority from U.S. Provisional Patent Application Ser. No. 61/072,768, filed Apr. 2, 2008.

FIELD OF THE INVENTION

The present invention generally relates to demulsifiers for use in industrial applications and, in particular, to demulsifiers comprising one or more anionic surfactants and/or non-ionic surfactants for use in pharmaceutical applications.

BACKGROUND OF THE INVENTION

Generally, preparing pharmaceuticals involves the extraction of the desired pharmaceutical from a liquid medium, typically a fermentation mixture. Extraction is necessary because the liquid medium may contain not only the desired pharmaceutical, but may also contain contaminants and impurities such as microorganisms, enzymes and other undesirable components. Typically, this process is carried out in industrial bioreactors through batch production or in continuous production.

Extraction of the desired pharmaceutical is typically accomplished in a multi-step process. After or shortly before adjusting the pH up or down as necessary, a solvent is added to the liquid medium, typically an organic phase such as amyl acetate, methyl ethyl ketone, amyl alcohol, butyl alcohol, benzyl alcohol or the like. The solvent is added to extract the desired pharmaceutical from the liquid medium to the organic phase. The liquid medium is then separated from the organic phase. However, this separation may be difficult to achieve as the liquid medium and organic phase often form an emulsion. Over time, the liquid medium and organic phase slowly separate themselves. More often, however, the addition of a demulsifier is desirable to encourage or speed up the separation of the phases.

After separation of the solvent phase and the liquid medium, the solvent phase is generally made up of the desired pharmaceutical, solvent, as well as trace amounts of impurities or contaminants. Conversely, the liquid medium is generally made the remaining impurities, contaminants and other undesirable components. There may also be trace amounts of the desired pharmaceutical remaining/dissolved in the liquid medium.

In addition, the solvent phase may be purified and decontaminated after separation from the water phase by, for example, the addition of purified water or passing the solvent through active carbon.

In a further step, the desired pharmaceutical can then be extracted from the solvent and into a water phase. One way this can be accomplished is by a re-adjustment of the pH of the mix. It is sometimes desirable to isolate a particular phase to more effectively isolate the pharmaceutical (e.g., precipitation of the active from water more easily achieved), among other reasons. Further, separation of the new water and solvent emulsion can be achieved through the similar aforementioned process. Excess solvent or water can be evaporated off, depending on the phase in which the pharmaceutical is maintained.

SUMMARY OF THE INVENTION

The present invention provides a demulsifier for use in a variety of industrial applications comprising one or more anionic surfactants, one or more non-ionic surfactants, or a combination thereof. It has been unexpectedly found that demulsifiers containing alkylsulfosuccinates, alkylsulfonates, alkylphosphonic acids, and their salts work effectively in pharmaceutical applications. In one embodiment, it has been found that a demulsifier comprising dioctyl sodium sulfosuccinate, sold under the trade name PENTEX 99™ (Rhodia Inc., Cranbury, N.J.), works effectively in pharmaceutical applications, for example, in the extraction of penicillin and derivates thereof. It is understood, however, that the demulsifier of the present invention can be utilized in the extraction of other pharmaceutical compositions. Typically, pharmaceutical compositions comprise an agent and a pharmaceutically acceptable carrier. The agent is present in an amount that is therapeutically effective, preferably in purified form. In one embodiment, the term "pharmaceutically acceptable" means approved by a regulatory agency of the Federal or a state government or listed in the U.S. Pharmacopeia or similar pharmacopeia.

One aspect of the present invention provides a demulsifier comprising: an anionic surfactant selected from the group consisting of alkylsulfosuccinates, alkylsulfonates, alkylphosphonic acids, salts thereof, and combinations thereof; a nonionic surfactant selected from the group consisting of ethylene oxide/propylene oxide copolymers, ethoxylated fatty acids of polyethylene glycol, terpene alkoxylates, modified alkanolamides, and combinations thereof; or a combination of one or more nonionic surfactant and anionic surfactant.

Another aspect of the present invention provides a demulsifier for use in pharmaceutical applications comprising: an anionic surfactant selected from the group consisting of alkylalkylsulfonates, succinates, alkylphosphonic acids, salts thereof, and combinations thereof. In one embodiment, the demulsifier comprises dioctyl sodium sulfosuccinate. In another embodiment, the demulsifier comprises an alkylsulfonate, typically an alkylsulfonate having from 5 to 25 carbon atoms, more typically having from 8 to 20 carbon atoms, and most typically having from 10 to 19 carbon atoms.

Another aspect of the present invention provides a demulsifier for use in pharmaceutical applications comprising a nonionic surfactant selected from the group consisting of ethylene oxide/propylene oxide copolymers, ethoxylated fatty acids of polyethylene glycol, terpene alkoxylates, modified alkanolamides, and combinations thereof.

In another aspect, the present invention is a method for breaking an emulsion produced in the preparation of pharmaceuticals comprising contacting the emulsion with a demulsifier comprising: (a) an anionic surfactant selected from the group consisting of alkylsulfosuccinates, alkylsulfonate, alkylphosphonic acids, salts thereof, and combinations thereof; (b) a nonionic surfactant selected from the group consisting of ethylene oxide/propylene oxide copolymers, ethoxylated fatty acids of polyethylene glycol, terpene alkoxylates, modified alkanolamides, and combinations thereof; or (c) a combination of (a) and (b).

In another aspect, the present invention is a method for breaking an emulsion produced in the preparation of pharmaceuticals comprising contacting the emulsion with a demulsifier comprising dioctyl sodium sulfosuccinate or a $C_{10}$-$C_{18}$ sulfonate. In one embodiment, the pharmaceutical is an antibiotic, typically, penicillin or derivatives thereof.

A further aspect of the present invention provides a demulsifier formulated with a relatively low surfactant levels compared to polymers for cost-effective performance.

DETAILED DESCRIPTION OF THE INVENTION

The present invention generally relates to demulsifiers for resolving or otherwise "breaking" emulsions that typically form during industrial applications including but not limited to pharmaceutical and home and beauty applications. More specifically, the present invention generally relates to solvent-in-oil demulsifiers having low toxicity and comprising one or more of an anionic surfactant, a nonionic surfactant or a combination thereof.

To aid in the understanding of the invention, the following non-limiting definitions are provided.

As used herein, "emulsion" shall mean a composition, usually liquid or gelled, comprising two or more immiscible phases in which a first phase (the "dispersed phase") is dispersed in a second phase (the "continuous phase"). Oil and water emulsions include water-in-oil emulsions (water dispersed in oil) and oil-in-water emulsions (oil dispersed in water). Similarly, solvent and water emulsions include solvent-in-water emulsions (solvent dispersed in water) and water-in-solvent emulsions (water dispersed in solvent). As used herein, any reference to "emulsion" shall be interpreted to apply equally to all aforementioned emulsions. Also as used herein, the term "inverse emulsion" refers to an oil-in-water or solvent-in-water emulsion.

The terms "surfactant" and "emulsifier" are interchangeable and generally refer to a wetting agent that lowers the surface or interfacial tension between two liquids. Using surfactants allows obtaining the dispersion of one phase in the other.

As used herein, the term "demulsifier" shall mean a surfactant, combination of surfactants or surfactant systems that inhibit or prevent dispersion in an emulsion, thereby permitting the immiscible substances to be more readily separated from one another.

The term "emulsion breaking" shall refer to the process of disrupting the stable surface between the continuous phase and dispersed phase of an emulsion. It is generally accepted that high molecular weight surfactants and water soluble polymers will displace lower molecular weight surfactants at a surface boundary. "Emulsion breakers" are designed to be similar in chemistry to emulsifying surfactants but have a significantly higher molecular weight, allowing them to disrupt the surface layer and destabilize the emulsion. See, e.g., Brady, J. E. and G. E. Humiston, *General Chemistry, Principles and Structure*, John Wiley and Sons, Inc., New York (1982).

The term "water" is used herein to mean water to prepare demulsifiers and water present in oil and water emulsions as well as oil and solvent emulsions. In addition, water may contain dissolved organic salts, organic acids, organic acid salts, inorganic salts, or combinations thereof. Examples are potassium chloride, ammonium chloride, and trimethylammonium chloride.

Useful surfactants include anionic and nonionic compounds, which may be used separately or as a mixture in a system, as described below in greater detail. Anionic and nonionic surfactants are added in concentrations that range preferably from about 50 parts per million ("ppm") to about ppm of the liquid component volume and more preferably from about 125 ppm to about 2000 ppm of the liquid component volume. The surfactants of the present invention may be used individually or in mixtures or systems.

The present invention provides, in one embodiment, a demulsifier comprising: an anionic surfactant selected from the group consisting of alkylsulfosuccinates, alkylsulfonate, alkylphosphonic acids, and salts thereof; a nonionic surfactant selected from the group consisting of ethylene oxide/propylene oxide copolymers, ethoxylated fatty acids of polyethylene glycol, terpene alkoxylates and modified alkanolamides; or a combination of one or more anionic surfactants and nonionic surfactants.

Combinations of surfactants may also be used in the present invention. In specific embodiments, the anionic surfactant may be present in amounts from about 5% to about 95% by weight of the total surfactant, and the nonionic surfactant may be present in amount from about 5% to about 95% by weight by weight of the total surfactant. In some embodiments the anionic surfactant is present from about 10% to about 80% by weight by weight of the total surfactant and the nonionic surfactant is present from about 10% to about 80% by weight by weight of the total surfactant.

Anionic Surfactants

Anionic surfactants useful in the demulsifier composition of the present invention include but are not limited to alkylsulfosuccinates, alkylsulfonates, alkylphosphonic acids, and their salts, and combinations thereof. In one embodiment, it has been found that dioctyl sodium sulfosuccinate and systems thereof, sold under the trade name PENTEX 99™ (Rhodia Inc., Cranbury, N.J.), are an effective demulsifiers in pharmaceutical applications. In particular, dioctyl sulfosuccinate and salts thereof including dioctyl sodium sulfosuccinate are effective demulsifiers in the extraction of penicillin. Anionic surfactants, and in particular, sulfosuccinates such as sodium dioctylsulfosuccinate, may be used in either powder form or in solution.

In another embodiment, anionic surfactants include, but are not limited to, aliphatic sulfonates, such as a primary alkane (e.g., $C_5$-$C_{25}$) sulfonates, primary alkane (e.g., $C_5$-$C_{25}$) disulfonates, ($C_5$-$C_{25}$)alkene sulfonates, $C_5$-$C_{25}$ hydroxyalkane sulfonates, alkyl glyceryl ether sulfonates (AGS), aromatic sulfonates such as alkyl benzene sulfonates. In one embodiment, the anionic surfactant is sodium $C_{10}$-$C_{20}$ olefin sulfonate, more typically sodium $C_{14}$-$C_{16}$ olefin sulfonate.

In another embodiment, the anionic surfactant comprises an alkylsulfonate, typically an alkylsulfonate having from 5 to 25 carbon atoms, more typically having from 8 to 20 carbon atoms, and most typically having from 10 to 19 carbon atoms.

In other embodiments of the invention, the anionic surfactant may be octylphosphonic acid, laurylphosphonic acid, salts of octylphosphonic acid, salts of laurylphosphonic acid, and combinations thereof.

Suitable anionic surfactants include the following structural formulas:

Alkyl Phosphonic Acid and Salts $$R^1PO_3M \quad\quad\quad (I)$$

In the above structure, $R^1$ is alkyl and may be branched or linear; "M" is hydrogen, an alkali metal such as sodium or potassium, or an ammonium salt; $R^1$ preferably contains 5 to 20 carbon atoms, more preferably 5 to 16 atoms, most preferably 8 to 12 carbon atoms.

Alkylsulfosuccinates

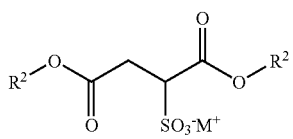
(II)

In the above structure $R^2$ is selected from the group consisting of alkyl, $-CH_2CH_2OH$, aryl, alkaryl, alkoxy, alkylarylalkyl, arylalkyl, alkylamidoalkyl and alkylaminoalkyl. In embodiments in which $R^2$ represents alkyl, the group preferably has about 5 to about 20 carbon atoms and more preferably has about 10 to about 18 carbon atoms. In embodiments in which $R^2$ represents aryl, the group preferably comprises a phenyl, diphenyl, diphenylether, or naphthalene moiety. "M" is hydrogen, an alkali metal such as sodium or potassium, or an ammonium salt. "M" is preferably an alkali metal such as sodium or potassium, more preferably sodium.

Nonionic Surfactants

Nonionic surfactants for use in the present invention include but are not limited to linear copolymers, block copolymers, and reverse copolymers of ethylene oxide/propylene oxide; ethoxylated fatty acids of polyethylene glycol/polypropylene glycol; fatty acid esters; glycerol esters; ethoxylated fatty acids esters of glycol; ethoxylated fatty acid esters of polyethylene glycol; terpene alkoxylates, modified alkanolamides and sorbitan esters.

Typical nonionic surfactants are ethylene oxide/propylene oxide copolymers, ethoxylated fatty acids esters of glycol, ethoxylated fatty acid esters of polyethylene glycol, terpene alkoxylates and modified alkanomides. More typical nonionic surfactants are ethylene oxide/propylene oxide copolymers, ethoxylated fatty acid esters of polyethylene glycol, terpene alkoxylates, and combinations thereof.

Suitable non-ionic surfactants include the surfactants having the structural formulas as shown below. Suitable ethylene oxide/propylene oxide copolymers may be selected from the group consisting of ethylene oxide/propylene oxide block copolymers, ethylene oxide/propylene oxide alkoxylates, and ethylene oxide/propylene oxide reverse copolymers.

Ethyleneoxide/Propyleneoxide Block Copolymer Surfactant

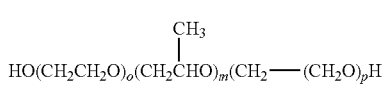
(III)

In certain embodiments "o," "m," and "n" are from about 1 to about 50. In alternative embodiments, the nonionic surfactant is the product sold under the trade name ANTAROX® L-64 (Rhodia Inc., Cranbury, N.J.).

Ethyleneoxide/Propyleneoxide Reverse Copolymer Surfactant

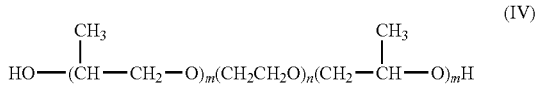
(IV)

In one embodiment "m" is from about 10 to 60 and "n" is about 0 to about 15. In one embodiment, "m" is about 27, and "n" is about 8. In an alternative embodiment, the nonionic surfactant is the product sold under the trade name ANTAROX® 31R1 (Rhodia Inc., Cranbury, N.J.).

Ethylene Oxide/Propylene Oxide Alkoxylates

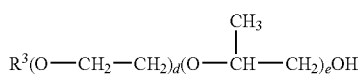
(V)

In one embodiment, "d" is from about 1 to about 10 and "e" is from about 1 to about 50. $R^3$ is a hydrocarbon chain hydrocarbon chain containing about 1 to about 22 carbon atoms and may be branched or straight-chained and saturated or unsaturated.

In another embodiment, "d" is about 5 and "e" is about 8. In an alternative embodiment, the nonionic surfactant is the product sold under the trade name ANTAROX® BL-14 (Rhodia Inc., Cranbury, N.J.).

Ethoxylated Fatty Acid Esters of Polyethylene Glycol

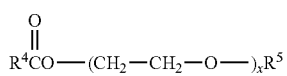
(VI)

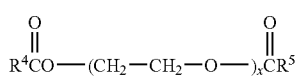
(VII)

In some embodiments $R^4$ is a hydrogen or a hydrocarbon chain containing about 10 to about 22 carbon atoms and may be branched or straight-chained and saturated or unsaturated and is selected from the group consisting of hydrogen, alkyl, alkoxy, aryl, alkaryl, alkylarylalkyl, arylalkyl, alkylamidoalkyl, and alkylaminoalkyl. $R^5$ is preferably a hydrocarbon chain containing about 1 to about 22 carbon atoms and may be branched or straight-chained and saturated or unsaturated and is selected from the group consisting of alkyl, alkoxy, aryl, alkaryl, alkylarylalkyl, arylalkyl, alkylamidoalkyl, and alkylaminoalkyl. In embodiments in which $R^4$ and $R^5$ represent alkyl, the groups preferably have about 5 to about 20 carbon atoms and more preferably have about 10 to about 18 carbon atoms. In embodiments in which $R^4$ and $R^5$ represent aryl, the groups preferably comprise a phenyl, diphenyl, diphenylether, or naphthalene moiety. In referred embodiments "x" is from about 1 to about 20. In certain embodiments the structures are mono and diesters.

In an alternative embodiment, the nonionic surfactants are the products of dioleate ester of PEG 400, sold under the trade name ALKAMUS® 400DO (Rhodia Inc., Cranbury, N.J.).

Terpene Alkoxylates

Terpene alkoxylates are terpene-based surfactants derived from a renewable raw materials such as α-pinene and β-pinene, and have a C-9 bicyclic alkyl hydrophobe and polyoxy alkylene units in an block distribution or intermixed in random or tapered distribution along the hydrophilic chain. The terpene alkoxylate surfactants are described in the U.S. Patent Application Publication No. 2006/0135683 to Adam al., Jun. 22, 2006, is incorporated herein by reference.

Typical terpene alkoxylates are Nopol alkoxylate surfactants and have the general formula:

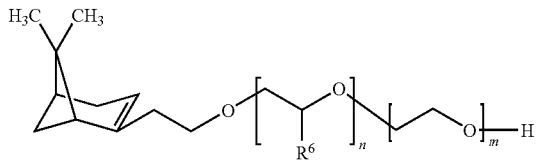
(VIII)

where $R^6$ is hydrogen, $CH_3$, or $C_2H_5$; "n" is from about 20 to about 30; "m" is from about 0 to about 20. The "n" and "m" units may be of block distribution or intermixed in random or tapered distribution along the chain.

In another embodiment, $R^6$ is $CH_3$; "n" is from about 20 to about 25; "m" is from about 5 to about 10.

In an alternative embodiment, the nonionic surfactant is the product sold under the trade name RHODOCLEAN® HP (Rhodia Inc., Cranbury, N.J.).

Modified Alkanolamides

The demulsifiers of the present invention contain modified alkanolamides as non ionic surfactant. In an embodiment the modified alkanolamide is the product sold under the trade name ANTAROX AG 5 (Rhodia Inc., Cranbury, N.J.).

Demulsifiers of the present invention may be used alone or in combination with any of a number of additional demulsifiers described herein or known in the art including but not limited to alkylphenol formaldehyde condensation products such as alkylphenol formaldehyde, resin alkoxylates, polyalkylene glycols including polypropylene glycols and crosslinked polypropylene glycols, organic sulfonates, alkoxylated alcohols, alkoxylated polyols, fatty acids, complex resin esters, alkoxylated fatty amines, alkoxylated polymeric amines, and the like. Thus, for example, the demulsifier may comprise an alkylsulfosuccinate such as sodium diisooctyl-sulfosuccinate and an ethylene oxide/propylene oxide copolymer. Alternatively, as an example, the demulsifier may comprise an alkylsulfosuccinate and an ethoxylated fatty acid of ethylene glycol.

The demulsifiers of the present invention may also be used in systems in combination with components such as organic solvents, viscosity reducers, and other chemical treatments used in industrial processing. Optionally, a variety of conventional additives that do not adversely affect the demulsifier performance can be used.

In an embodiment of the invention a demulsifier composition is prepared by mixing water with a surfactant comprising an anionic surfactant, a nonionic surfactant, or combinations thereof. The water utilized for forming the demulsifier of this invention can be fresh water or salt water. In addition the water may contain dissolved organic salts, organic acids, organic acid salts, inorganic salts, or combinations thereof. The demulsifier may contain one or more organic solvents. Isopropyl alcohol is one example of a suitable organic solvent. Standard mixing procedures known in the art can be employed since heating of the solution and special agitation conditions are normally not necessary. In one embodiment, a demulsifier composition comprises a surfactant present from about 60% to about 100% by weight of the composition, propylene glycol present from about 0% to about 2% by weight of the composition, isopropyl alcohol present from about 0% to about 2% by weight of the composition, and water. Typically, the surfactant is from about 70% to about 80% by weight of the composition.

In another embodiment of the invention the initial pH of the demulsifier composition may be lowered or raised to impart stability or to aid in the partitioning of the desired pharmaceutical. The decrease of pH may be by brought about by adding acid and/or buffers. Similarly, it may be suitable to add a base and/or buffers to increase the pH of the demulsifier composition.

The present invention further provides a method for breaking an emulsion produced in the preparation of pharmaceuticals. The emulsion typically comprises oil and water or solvent and water. The method includes contacting the emulsion with any of the demulsifiers described herein or any combinations of such demulsifiers. One or more of above-mentioned demulsifiers are surprisingly effective in breaking emulsions produced in preparation of certain pharmaceuticals such an antibiotics, including in particular, penicillin or substances obtained from fungus (e.g, streptomycin, efrotomycin), by fermentation. In one embodiment, demulsifiers comprising dioctyl sodium sulfosuccinate have been found to be particularly effective in phase separation with a well defined interface, wherein substantially or substantially all of the desired pharmaceutical was segregated into one of the phases chosen by manufacturer. The phase in which the desired pharmaceutical is maintained depends in large part on manipulation of the pH. For example, a low pH adjustment (i.e., acidic) may cause the desired pharmaceutical to collect in the organic phase, whereas a higher pH adjustment (i.e., neutral or basic) may cause the desired pharmaceutical to collect in the water phase.

Consequently, the method comprises contacting the emulsion with a demulsifier comprising an anionic surfactant selected from the group consisting of alkylsulfosuccinates, alkylphosphonic acids, and salts of alkylphosphonic acids; a nonionic surfactant selected from the group consisting of ethylene oxide/propylene oxide copolymers, ethoxylated fatty acids of polyethylene glycol, terpene alkoxylates, and modified alkanolamides; or a combination of at least one anionic surfactant and nonionic surfactant. For example, the method may include contacting an emulsion with a demulsifier composed of an alkylsulfosuccinate such as dioctyl sodium sulfosuccinate and an ethylene oxide/propylene oxide copolymer. Alternatively, the method may also include contacting the emulsion with the demulsifier composed of an alkylsulfosuccinate and an ethoxylated fatty acid of ethylene glycol.

In one embodiment, the demulsifier is comprised of dioctyl sodium sulfosuccinate (sold under the trade name PENTEX 99™ (Rhodia Inc., Cranbury, N.J.).

For example, in one embodiment, pH of the mixture is adjusted to below a pH of 4 using any acceptable acid including but not limited to sulfuric acid and citric acid. Either shortly before or shortly after the pH adjustment, an extracting solvent including but not limited to amyl acetate, methyl ethyl ketone, methyl isobutyl ketone, amyl alcohol, butyl acetate, butyl alcohol, benzyl alcohol or the like, is added to extract the desired pharmaceutical from the water phase to the solvent. The process is typically run at a process temperature of between about 5° C. to about 50° C. At the present stage, most or a substantial part of the pharmaceutical is separated into the solvent. The solvent is optionally cleaned by filtering the solvent through a mixture of activated/active carbon.

The next step can be employed by adjusting the pH of the mixture to a neutral or basic pH, which is typically between about 7 to about 9. Water is then added to the solvent with the desired pharmaceutical to form a second emulsion. The desired pharmaceutical can thus be separated from the solvent and into the added water (separation may be accomplished as described above for the first step emulsion). The demulsifier comprising the present invention can be added at any time during the process, including but not limited to during, before or after the first emulsion and/or second emulsion.

In a further embodiment, the method includes dispersing the demulsifier in a suitable solvent or liquid carrier. Representative solvents and carriers include aromatic hydrocarbons, aliphatic hydrocarbons such as kerosene, glycols, glycol ethers, alcohols, water, hydrocarbons, aromatic solvents, fatty acid methyl esters, similar compounds, and combinations thereof. The liquid carrier may then be applied to the emulsion by any suitable process commonly known in the art.

Although the invention herein has been described with reference to particular embodiments and examples, it is to be understood that these embodiments are merely illustrative of the principles and applications of the present invention. Other embodiments have been suggested and still others may occur to those skilled in the art upon a reading and understanding of the specification. It is intended that all such embodiments be included within the scope of this invention. It is therefore to be understood that numerous modifications may be made to the illustrative embodiments and that other arrangements may be devised without departing from the spirit and scope of the present invention as defined by the claims.

We claim:

1. A composition comprising a pharmaceutical and a demulsifier comprising: an anionic surfactant selected from the group consisting of alkylsulfosuccinates, alkylsulfonates, alkylphosphonic acids, salts thereof, and combinations thereof; and a nonionic surfactant selected from the group consisting of ethylene oxide/propylene oxide copolymers, ethoxylated fatty acid esters of polyethylene glycol, terpene alkoxylates, modified alkanomides, and combinations thereof.

2. The composition of claim 1 wherein the anionic surfactant is present from about 5% to about 95% by weight of the total surfactant.

3. The composition of claim 1 wherein the nonionic surfactant is present from about 5% to about 95% by weight of the total surfactant.

4. The composition of claim 1 wherein the anionic surfactant is present from about 10% to about 80% by weight of the total surfactant.

5. The composition of claim 1 wherein the nonionic surfactant is present from about 10% to about 80% by weight of the total surfactant.

6. The composition of claim 1 wherein the anionic surfactant is sodium dioctylsulfosuccinate.

7. The composition of claim 1 wherein the anionic surfactant is an alkylsulfonate having from 10 to 18 carbon atoms.

8. The composition of claim 1 wherein the anionic surfactant is selected from the group consisting of octylphosphonic acid, laurylphosphonic acid, salts thereof, and combinations thereof.

9. The composition of claim 1 wherein the nonionic surfactant is an ethylene oxide/propylene oxide copolymer selected from the group consisting of ethylene oxide/propylene oxide alkoxylates, ethylene oxide/propylene oxide block copolymers, and ethylene oxide/propylene oxide reverse copolymers.

10. The composition of claim 9 wherein the nonionic surfactant is an ethylene oxide/propylene oxide block copolymer of the general formula:

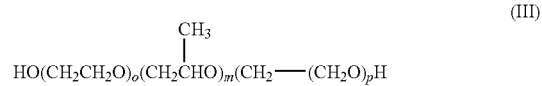

wherein "m" is from about 1 to about 50, "o" and "p" are each from about 1 to about 20.

11. The composition of claim 9 wherein the nonionic surfactant is an ethylene oxide/propylene oxide reverse copolymer of the general formula:

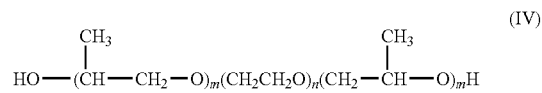

wherein "m" is from about 10 to about 60, and "n" is from about 0 to about 15.

12. The composition of claim 11 wherein "m" is about 27 and "n" is about 8.

13. A demulsifier composition useful for demulsifying a pharmaceutical composition of claim 9 comprising an anionic surfactant selected from the group consisting of alkylsulfosuccinates, alkylsulfonates, alkylphosphonic acids, salts thereof, and combinations thereof; and a nonionic surfactant which is an ethylene oxide/propylene oxide alkoxylate having the following formula:

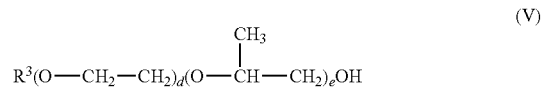

wherein "d" is about 5 and "e" is about 8, and $R^3$ is a hydrocarbon chain containing from about 1 to about 22 carbon atoms.

14. A demulsifier composition useful for demulsifying a pharmaceutical composition comprising an anionic surfactant selected from the group consisting of alkylsulfosuccinates, alkylsulfonates, alkylphosphonic acids, salts thereof, and combinations thereof; and a non-ionic surfactant is a terpene alkoxylate having the following formula:

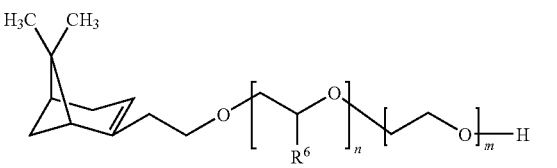

wherein R6 is methyl or ethyl, "n" is from about 20 to about 30, and "m" is from 0 to about 20.

15. The composition of claim 14, wherein $R^6$ is methyl, "n" is from about 20 to 25, and "m" is from about 5 to about 10.

16. The composition of claim 1 wherein the nonionic surfactant is an ethoxylated fatty acid esters of polyethylene glycol of the general formulae:

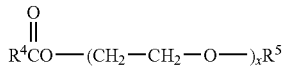
(VI)

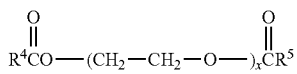
(VII)

wherein "x" is from about 1 to about 20, R4 is a hydrocarbon chain containing about 10 to 22 carbon atoms, and R5 is a hydrogen or a hydrocarbon chain containing about 1 to about 20 carbon atoms.

17. A demulsifier composition useful for demulsifying a pharmaceutical composition comprising an anionic surfactant selected from the group consisting of alkylsulfosuccinates, alkylsulfonates, alkylphosphonic acids, salts thereof, and combinations thereof; and a terpene alkoxylate having the following formula:

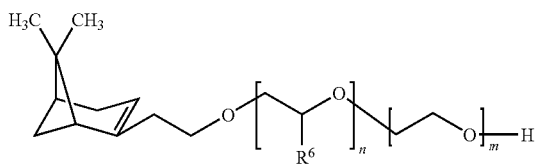
(VIII)

wherein R6 is methyl or ethyl, "n" is from about 20 to about 30, and "m" is from 0 to about 20.

18. A method for breaking an emulsion produced in the preparation of pharmaceuticals, the emulsion comprising a pharmaceutical, comprising contacting the emulsion with a demulsifier comprising
  (a) an anionic surfactant selected from the group consisting of alkylsulfosuccinates, alkylsulfonates, alkylphosphonic acids, salts thereof, and combinations thereof;
  (b) a nonionic surfactant selected from the group consisting of ethylene oxide/propylene oxide copolymers, ethoxylated fatty acids of polyethylene glycol, terpene alkoxylates, modified alkanolamides, and combinations thereof; or
  (c) a combination of (a) and (b).

19. The method of claim 18 wherein the anionic surfactant is sodium dioctyl sulfosuccinate, an alkylsulfonate having 10 to 18 carbon atoms or sodium C10-C20 olefin sulfonate.

20. The method of claim 18 further comprising dispensing the demulsifier in a suitable solvent system prior to contacting the demulsifier with the emulsion.

21. The method of claim 20 wherein the solvent system comprises glycols, glycol ethers, alcohols, water, hydrocarbons, aromatic solvents, fatty acid methyl esters, and combinations thereof.

22. The method of claim 18 wherein the emulsion is a water-in-solvent emulsion.

23. The method of claim 18 wherein the nonionic surfactant is an ethylene oxide/propylene oxide copolymer selected from the group consisting of ethylene oxide/propylene oxide alkoxylates, ethylene oxide/propylene oxide block copolymers, and ethylene oxide/propylene oxide reverse copolymers.

24. The method of claim 23 wherein the terpene alkoxylate has the following formula:

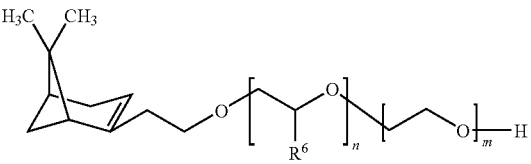
(VIII)

wherein R6 is methyl or ethyl, "n" is from about 20 to about 30, and "m" is from 0 to about 20.

25. The composition of claim 1 wherein the anionic surfactant comprises sodium $C_{10}$-$C_{20}$ olefin sulfonate.

* * * * *